United States Patent
Banik et al.

(10) Patent No.: US 6,540,720 B1
(45) Date of Patent: Apr. 1, 2003

(54) MINIATURE X-RAY UNIT

(75) Inventors: Michael S. Banik, Bolton, MA (US); Marcia McBride Sakal, Bolton, MA (US)

(73) Assignee: SciMed Life Systems, Inc., Maple Grove, MN (US)

( * ) Notice: Subject to any disclaimer, the term of this patent is extended or adjusted under 35 U.S.C. 154(b) by 212 days.

(21) Appl. No.: 09/709,670

(22) Filed: Nov. 10, 2000

(51) Int. Cl.[7] .............................................. A61M 37/00
(52) U.S. Cl. ....................... 604/103.01; 604/20; 604/21; 600/3
(58) Field of Search .................. 604/103.01, 19, 604/20, 21, 22; 600/1, 3, 7, 8; 378/65

(56) References Cited

U.S. PATENT DOCUMENTS

| | | | |
|---|---|---|---|
| 4,641,649 A | 2/1987 | Walinsky et al. | |
| 4,652,846 A | 3/1987 | Sobottka | |
| 4,860,744 A | 8/1989 | Johnson et al. | |
| 4,993,404 A | 2/1991 | Lane | |
| 5,006,119 A | 4/1991 | Acker et al. | |
| 5,026,367 A * | 6/1991 | Leckrone et al. | 604/21 |
| 5,041,107 A | 8/1991 | Heil, Jr. | |
| 5,084,061 A | 1/1992 | Gau et al. | |
| 5,127,394 A | 7/1992 | Lane | |
| 5,151,100 A | 9/1992 | Abele et al. | |
| 5,230,349 A | 7/1993 | Langberg | |
| 5,246,437 A * | 9/1993 | Abela | 604/21 |
| 5,354,220 A | 10/1994 | Ganguly et al. | |
| 5,372,603 A | 12/1994 | Acker et al. | |
| 5,395,362 A * | 3/1995 | Sacharoff et al. | 604/20 |
| 5,542,928 A | 8/1996 | Evans et al. | |
| 5,562,633 A | 10/1996 | Wozencroft | |
| 5,566,221 A | 10/1996 | Smith et al. | |
| 5,591,162 A | 1/1997 | Fletcher et al. | |
| 5,599,346 A | 2/1997 | Edwards et al. | |
| 5,704,914 A | 1/1998 | Stocking et al. | |
| 5,718,688 A | 2/1998 | Wozendroft | |
| 5,720,720 A * | 2/1998 | Laske et al. | 604/21 |
| 5,782,740 A | 7/1998 | Schneiderman | |
| 5,793,272 A | 8/1998 | Burghartz et al. | |
| 5,795,339 A | 8/1998 | Erskine | |
| 5,816,999 A | 10/1998 | Bischoff et al | |
| 5,865,806 A | 2/1999 | Howell | |
| 6,061,587 A * | 5/2000 | Kucharczyk et al. | 604/21 |
| 6,135,997 A * | 10/2000 | Laufer et al. | 604/20 |
| 6,183,410 B1 * | 2/2001 | Jacobsen et al. | 600/3 |
| 6,319,188 B1 * | 11/2001 | Lovoi | 600/3 |

FOREIGN PATENT DOCUMENTS

| | | |
|---|---|---|
| WO | 97/07740 | 3/1997 |
| WO | 98/48899 | 11/1998 |
| WO | 00/09212 | 2/2000 |

* cited by examiner

*Primary Examiner*—Teresa Walberg
*Assistant Examiner*—Fadi H. Dahbour
(74) *Attorney, Agent, or Firm*—Fulbright & Jaworski L.L.P.

(57) ABSTRACT

An x-ray catheter being a tapered bead can penetrate tumors and deliver x-rays direct from an x-ray source therein to the target tissue, reducing or eliminating irradiation of healthy tissue.

10 Claims, 4 Drawing Sheets

FIG. 3
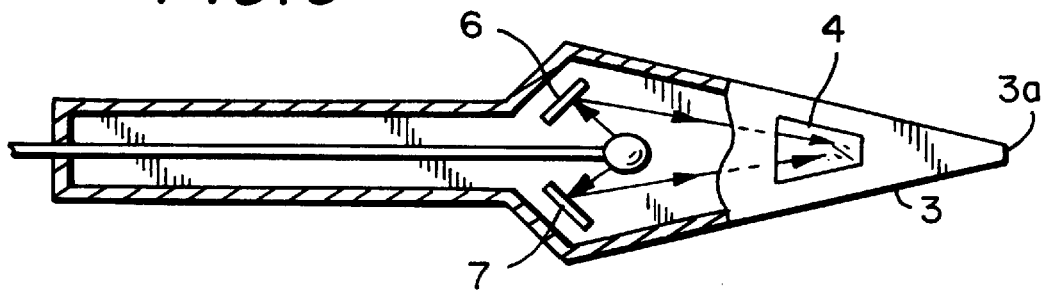
FIG. 4
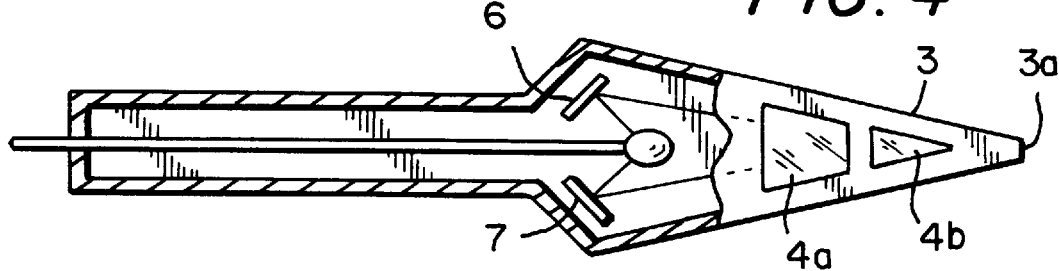
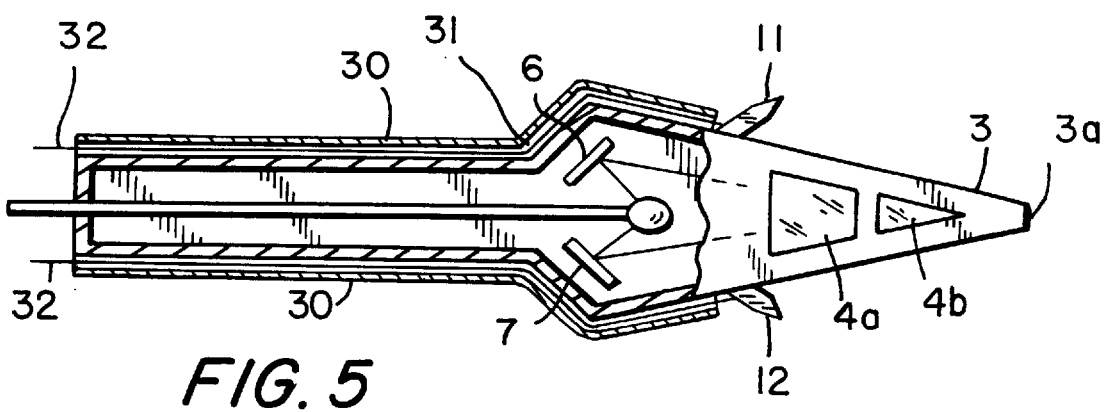
FIG. 5

MINIATURE X-RAY UNIT

FIELD OF THE INVENTION

The invention relates to a miniaturized x-ray source situated in a catheter that generates x-rays while minimizing risk of exposure to the x-rays.

BACKGROUND OF THE INVENTION

Traditionally, x-rays have been used in the medical industry to view bone, tissue and teeth. X-rays have also been used to treat cancerous and precancerous conditions by exposing a patient to x-rays using an external x-ray source. Treatment of cancer with x-rays presents many well documented side effects, many of which are due to the broad exposure of the patient to the therapeutic x-rays.

Minimally invasive endoscopic techniques have been developed and are used to treat a variety of conditions. Endoluminal procedures are procedures performed with an endoscope, a tubular device into the lumen of which may be inserted a variety of rigid or flexible tools to treat or diagnose a patient's condition.

The desire for improved minimally invasive medical devices and techniques have led to the development of miniaturized x-ray devices that may be used in the treatment or prevention of a variety of medical conditions. International Publication No. WO 98/48899 discloses a miniature x-ray unit having an anode and cathode separated by a vacuum gap positioned inside a metal housing. The anode includes abase portion and a projecting portion. The x-ray unit is insulated and connected to a coaxial cable which, in turn, is connected to the power source. An x-ray window surrounds the projecting portion of the anode and the cathode so that the x-rays can exit the unit. The x-ray unit is sized for intra-vascular insertion, and may be used, inter alia, in vascular brachytherapy of coronary arteries, particularly after balloon angioplasty.

International Publication No. WO 97/07740 discloses an x-ray catheter having a catheter shaft with an x-ray unit attached to the distal end of the catheter shaft. The x-ray unit comprises an anode and a cathode coupled to an insulator to define a vacuum chamber. The x-ray unit is coupled to a voltage source via a coaxial cable. The x-ray unit can have a diameter of less than 4 mm and a length of less than about 15 mm, and can be used in conjunction with coronary angioplasty to prevent restenosis.

U.S. Pat. No. 5,084,061 discloses an intragastric balloon with improved valve locating means. The balloon has an ellipsoid or like configuration so that the balloon implanted in the stomach tends to rotate or rock only about one axis when a surgeon attempts to manipulate the balloon, for example, for the purpose of finding a filler valve and inserting a filler tube into it. For easy location, the filler valve is disposed on the equator. A retrieval tab is mounted to the exterior of the balloon, to permit capturing of the balloon and retrieval from the stomach, after the balloon has been deflated and is no longer desired for weight control purposes. Visual and x-ray opaque markers are located in the proximity of the valve and of the retrieval tab to facilitate their visualization with an endoscopic light when the balloon is in the stomach.

U.S. Pat. No. 5,127,394 describes a fluoroscopy-switching device and method for preventing accidental over radiation of a patient in surgical procedures involving both fluoroscopy and endoscopy. Video outputs from the endoscope and fluoroscope is connected to a switching device. The endoscope generates a video signal having a first video format, and the fluoroscope generates a video signal having a second video format. The physician uses the switching device to select from between the endoscope video output and the fluoroscope video output for viewing on a video monitor which accepts a video signal of a predetermined video format. The switching device is operable to convert at least one of the endoscope video signal or the fluoroscope video signal to the predetermined video format, which the monitor accepts. When the endoscope video output is selected for viewing, the switching device automatically deactivates the x-ray generator of the fluoroscope. When the switching device is actuated to select the fluoroscope video signal for viewing on the monitor, the switching device automatically reactivates the x-ray generator. In this manner, over radiation of the patient during periods when the fluoroscope is not being used.

U.S. Pat. No. 4,993,404 describes a fluoroscopy-switching device for preventing accidental over radiation of a patient in surgical procedures involving both fluoroscopy and endoscopy. Video outputs from the fluoroscope and endoscope is connected to a switching device. The physician uses the switching device to select from between the endoscope video output and the fluoroscope video output for viewing on a video monitor. When the endoscope video output is selected for viewing, the switching device automatically deactivates the x-ray generator of the fluoroscope. When the switching device is actuated to select the fluoroscope video signal for viewing on the monitor, the switching device automatically reactivates the x-ray generator. In this manner, over radiation of the patient during periods when the fluoroscope is not being used is avoided.

Miniaturized x-rays are not foolproof, however, and still present difficulties. The x-ray unit generates heat, which can damage adjacent tissue. Additionally, x-rays are not localized and irradiate local tissue rather than only irradiating the desired site. Also, it is difficult to maintain the positioning of these instruments inside at the desired location. Improved miniaturized x-ray units the overcome these difficulties are desirable.

Other techniques are used to treat tumors with x-rays, including planting a seed of radioactive material at the tumor site, typically accomplished with endoluminal procedures. However, the patient becomes "hot", i.e., radioactive, and the procedure risks exposure of the medical personnel to radiation exposure.

As noted above, many types of cancerous and precancerous conditions are treated by irradiating the tumor or site with x-rays. However, the x-rays are broadcast over a large area of healthy tissue in addition to the tumor, since the radiation is administered from outside the body so that it penetrates the skin and any internal organs or tissue to reach the desired site. To avoid this, miniaturized x-ray systems which generate x-rays at the desired site are a desirable alternative to conventional apparatus.

Many types of cancer occur in a body cavity or lumen, such as in the rectum, vagina, esophagus or pulmonary passages. It would be desirable to treat these cancers using miniaturized x-ray sources in combination with endoscopic techniques, which are minimally invasive to the patient, so that the cancer or other intraluminal tissue is directly treated with x-rays. This technique would minimize exposure of health tissues to the x-rays.

One problem with such devices and techniques is proper placement of the x-ray source is correct within the lumen.

This problem leads to the additional concern of how to insure the delivery of the correct dose of the x-ray source. Providing an electronically controlled x-ray source into a lumen would require a precise means for determining the placement as well as the dose of the x-ray. What is required is a solution to this problem.

Another problem is with use of x-rays to kill lesions that are located behind the surface of healthy tissue regions in the body. This may require killing healthy tissue since the healthy tissue is also exposed to the x-rays.

Another difficulty arises between x-ray dose and thickness of the target tissue or tumor. With thicker lesions, the x-ray source has to be larger and more powerful to penetrate the tissue. However, as the x-ray dose is increased, so is the size of the device and its associated power and heating concerns.

The present invention overcomes the difficulties associated with x-ray therapy and apparatus of the prior art by providing an endoscopic x-ray device that generates x-rays at the site of treatment and minimizes exposure of other tissues to irradiation.

SUMMARY OF THE INVENTION

The present invention relates to an x-ray device having a tapered or pointed tip having an x-ray source therein. The x-ray device can penetrate into tissue inside a body lumen to deliver x-rays to the target tissue while minimizing irradiation of surrounding tissue. The device is described in more detail below, with reference to the accompanying drawings which illustrate preferred embodiments of the invention.

BRIEF DESCRIPTION OF THE DRAWINGS

FIG. 3 is a plan view of a preferred device, showing a preferred electrode arrangement for the x-ray source.

FIG. 4 is a preferred device having multiple x-ray transparent windows.

FIG. 5 is a preferred x-ray device having drug delivery needles to deliver therapeutic or contrasting agents to target tissue.

DETAILED DESCRIPTION

Figure 1:
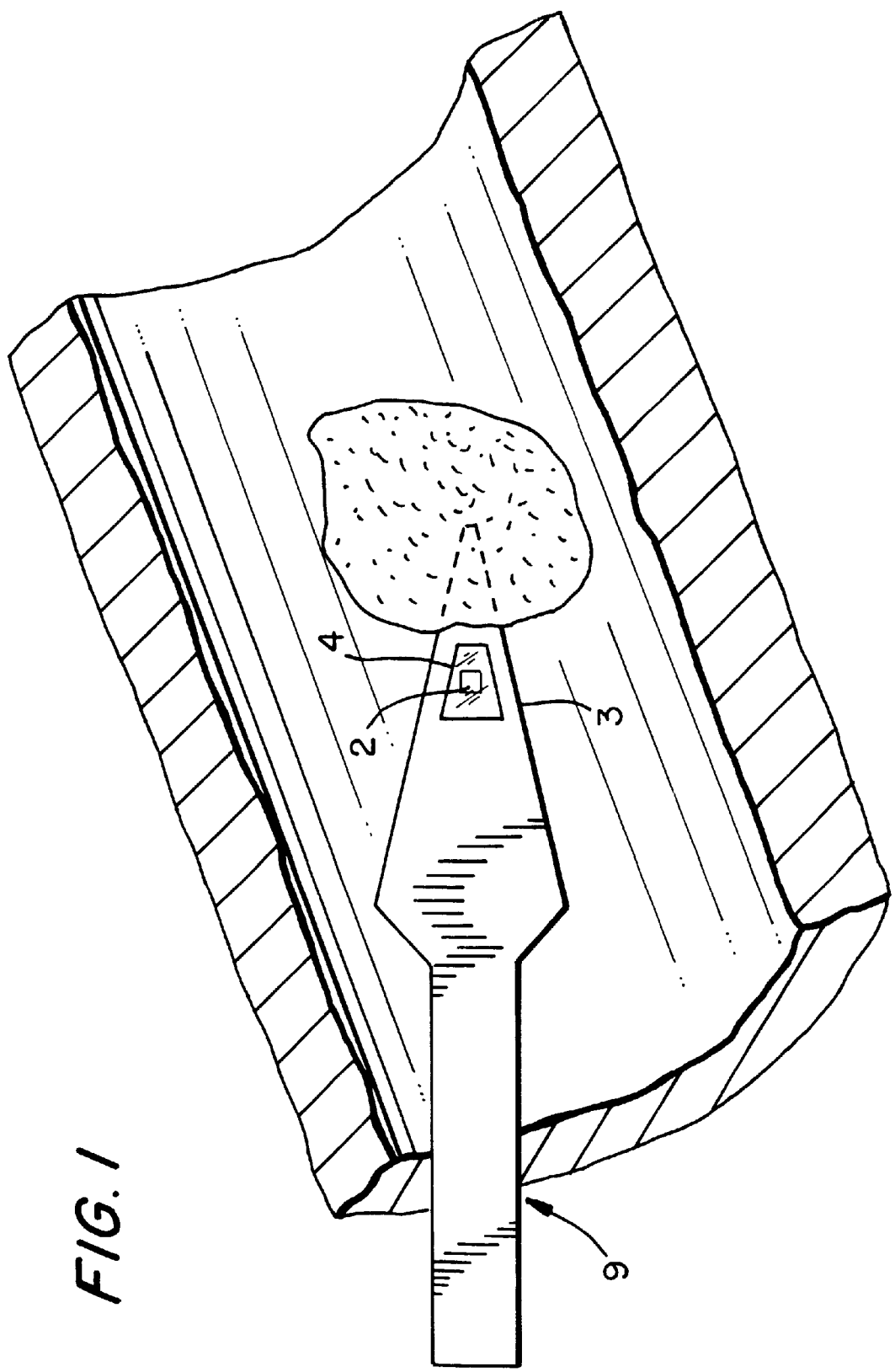
FIG. 1 is a preferred device of the invention shown inside a body lumen.
Figure 2:
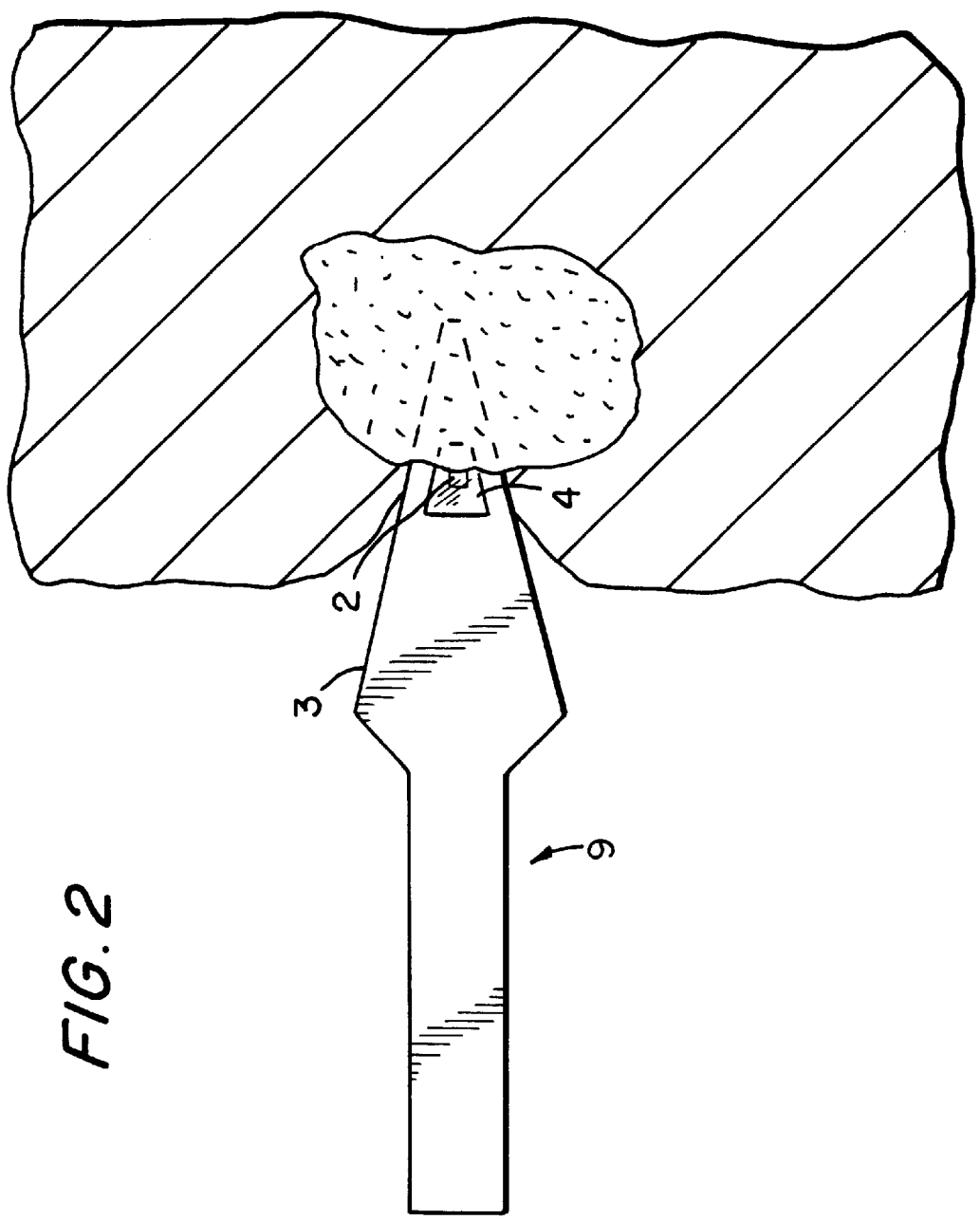
FIG. 2 shows the device of FIG. 1 after penetration into target tissue, in this case a tumor.

Referring to FIG. 1, x-ray source 2 is positioned inside an x-ray shielded head 3 at the distal end of x-ray catheter 9. Window 4 is located in the head. A portion of the shield may cover window 4 and is movable by an operator with an operably connected manual control system. Window 4 is made of x-ray transparent material such as lead free glass or plastic. Other suitable materials include beryllium, ceramic, and mica. Additional coatings of metal or insulating material may be layered or coated on the window material as needed. Correct alignment of window 4 to the tumor or target tissue exposes x-rays to the desired site, with substantially no irradiation of healthy tissue. X-ray head 3 has a pointed tip 3a, which allows penetration into target tissue upon manual operation. Penetration of pointed tip 3a allows delivery of x-rays to deep tissue without substantially effecting surface tissue, which is important in cases where the tumor is buried behind healthy tissue or with thick tumorous regions that needs irradiation throughout its depth as shown in FIG. 2.

The device of the present invention allows exposure of entire depth of thick tumors without adding more power or higher x-ray dosages, both of which may be unsafe for the patient. With the device, one can also penetrate healthy tissue to deliver x-rays to underlying target tissue.

Electrodes, preferably "shaped" electrodes 6, 7 as shown in FIGS. 3 to 8 are used to direct the x-rays inside the device. Electric power from an electric power source (not shown) provides electric energy to an electrode 6, 7 to generate x-rays. Preferably, electrodes 6, 7 are shaped to control of the direction of x-rays inside the device. By controlling of the x-ray direction, along with the window control directing the x-rays outside the device, allows for precise delivery of x-rays to target tissue. As shown in FIG. 4, multiple windows 4a, 4b in the shield to allow exposure in multiple "directed" regions simultaneously.

As shown in FIG. 5c drug delivery system 10 may be also provided. The drug delivery device includes needles 11, 12 which in this case are hollow with an opening at a distal end to allow for release of diagnostic and therapeutic agents, are retractably connected to x-ray head 3. Needles 11, 12 communicate with a reservoir that contains therapeutic or diagnostic agents so that these may be injected into the site. Any number of needles may be provided.

Outer wall 30 is provided and form a lumen 21 through which a retraction wire 32 or hollow drug delivery tube reside. This drug delivery system is used to inject drugs that may help heal the puncture wounds caused by the device or the drug delivery system is used to help the tumorous tissue absorb the x-rays. Also this drug delivery system is used to highlight the region.

Figure 6:
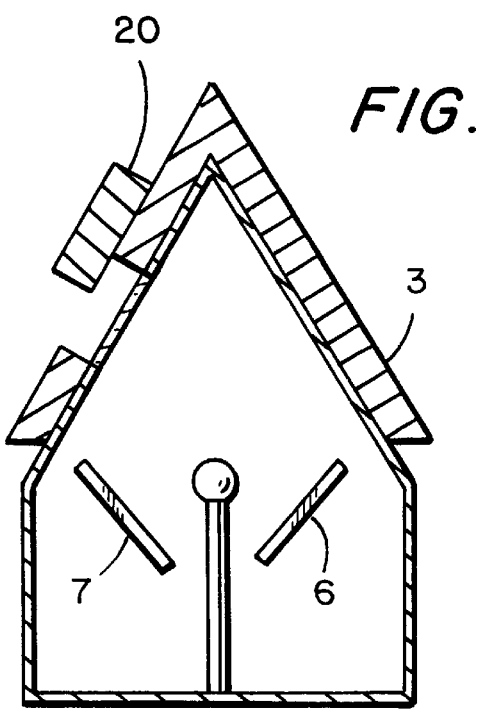
FIG. 6 is a cut-away view of a head portion of the device showing the x-ray source and a shield window and the electrodes position in relation thereto.
Figure 7:
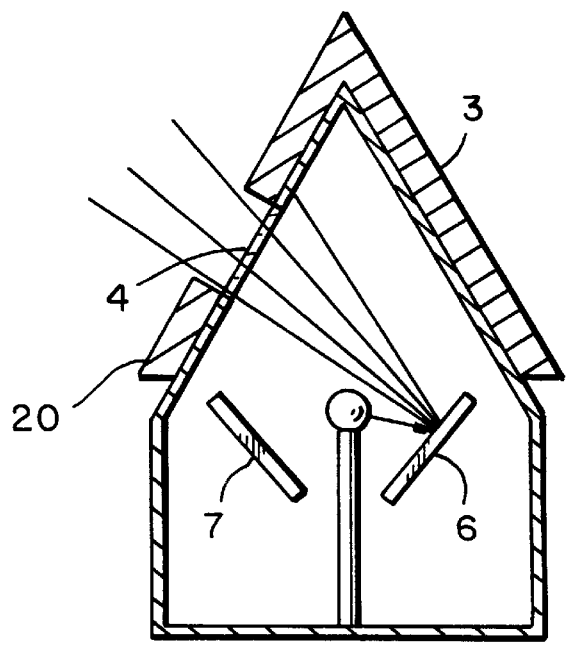
FIG. 7 is a plan view of an alternative head portion of the x-ray catheter, showing a slidable window which retracts to open and close an aperture through which x-rays may pass.
Figure 8:
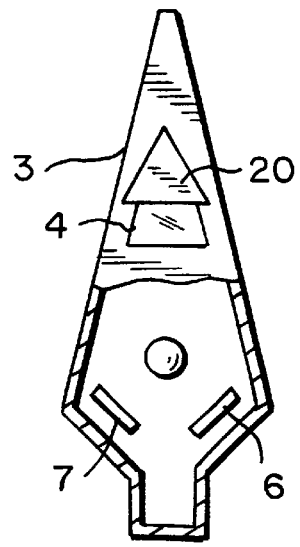
FIG. 8 is an expanded cut-away view of the x-ray catheter head of FIG. 7.

Aperture window as shown in FIG. 6 has an overlapped shield window is used to control the final position of the x-rays. Shield 20 is rotatable or slidable and is used to control the final window size. By sliding shield 20 over a window the overall window size is reduced, thus controlling the final window size, and hence the dosage and direction of exposure. These shields can be configured for specific types of procedures. The shields are easily removable to allow customization of the device prior to treatment. FIGS. 7 and 8 show the operation in detail.

The present invention also relates to methods of treatment, prophylaxis and adjunctive therapy using the miniaturized x-ray apparatus of the present invention. Suitable for use with other endoscopic equipment, the x-ray device is of an appropriate size such that it may be used to treat cancers of bodily lumens such as colorectal cancer, vaginal cancer, esophageal cancer, pulmonary cancers such as lung cancers, stomach cancer, oral cancers, or any cancer accessible by a bodily lumen by positioning the device adjacent the target tissue and irradiating the tissue with a therapeutically effective amount of x-rays. In similar fashion, one can treat pre-cancerous conditions or conditions related with cancer such as gastroesophageal reflux disease (GERD). Preferably, the selected site is illuminated prior to irradiation such that field of irradiated tissue is determined prior to irradiation of the site.

The apparatus of the invention may be used in conjunction with imaging devices such as visual, x-ray, magnetic or ultrasound to aid in positioning of the device inside a body lumen.

Although the present invention has been shown and described with respect to several preferred embodiments thereof, additional embodiments will be apparent to the skilled artisan without departing from the spirit and scope of the invention.

All cited references are incorporated herein by reference in their entireties.

Other embodiments will be apparent to those skilled in the art and are meant to be encompassed by the claim appended hereto.

What is claimed is:

1. An x-ray device comprising:
a catheter having a distal end and a proximal end, the distal end being tapered to a point and having an x-ray source therein, said tapered point capable of penetrating tissue upon application of sufficient force.

2. An x-ray device comprising;
a pointed x-ray shielded head having an x-ray transparent window therein; and
an x-ray source provided within said head adjacent to the x-ray transparent window.

3. The x-ray device of claim 2, further comprising an outer wall that forms a lumen with said head retractable needles retractably affixed on said head; and
a retractable wire in said lumen that is operably connected to said retractable needles.

4. The x-ray device of claim 3, wherein said head has hollow cavities therein into which the retractable needles retract.

5. The x-ray device of claim 3, wherein said needles are steel.

6. The x-ray device of claim 3, wherein said needles are connected via ducts to a reservoir containing a diagnostic or therapeutic agent.

7. The x-ray device of claim 6, wherein the needles are steel.

8. The x-ray device of claim 2, wherein retractable shutters are provided over said x-ray window.

9. The x-ray device of claim 2, having a plurality of x-ray transparent windows.

10. The x-ray device of claim 2, wherein said x-ray transparent window comprises at least one member selected from the group consisting of beryllium, glass, ceramic, plastic, and mica.

* * * * *